US012629102B2

(12) United States Patent
Webster et al.

(10) Patent No.: US 12,629,102 B2
(45) Date of Patent: May 19, 2026

(54) MANAGING CARDIAC RISK BASED ON PHYSIOLOGICAL MARKERS

(71) Applicant: WEST AFFUM HOLDINGS DAC, Dublin (IE)

(72) Inventors: Brian D. Webster, Mercer Island, WA (US); Cameron G. Pollock, Kirkland, WA (US); Laura M. Gustavson, Redmond, WA (US); Pamela F. Breske, Newcastle, WA (US); Zoie R. Engman, Kirkland, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 215 days.

(21) Appl. No.: 17/507,573

(22) Filed: Oct. 21, 2021

(65) Prior Publication Data
US 2022/0192605 A1     Jun. 23, 2022

Related U.S. Application Data

(60) Provisional application No. 63/129,547, filed on Dec. 22, 2020.

(51) Int. Cl.
A61B 5/00          (2006.01)
A61B 5/0205       (2006.01)
(Continued)

(52) U.S. Cl.
CPC .......... A61B 5/7275 (2013.01); A61B 5/0205 (2013.01); A61B 5/1118 (2013.01);
(Continued)

(58) Field of Classification Search
CPC ... A61B 5/7275; A61B 5/0205; A61B 5/1118; A61B 5/746
See application file for complete search history.

(56) References Cited

U.S. PATENT DOCUMENTS

| | | | |
|---|---|---|---|
| 3,724,355 A | 4/1973 | Busch et al. | |
| 3,724,455 A | 4/1973 | Unger | |

(Continued)

FOREIGN PATENT DOCUMENTS

| | | | |
|---|---|---|---|
| DE | 102005060985 A1 | 6/2007 | |
| EP | 2305110 A1 | 4/2011 | |

(Continued)

OTHER PUBLICATIONS

Ashley Burch et al.,. Decline in physical activity in the weeks preceding sustained ventricular arrhythmia in women. Heart Rhythm O2. Jun. 25, 2020;1(4):283-287. doi: 10.1016/j.hroo.2020.06.004. PMID: 34113882; PMCID: PMC8183853.*

(Continued)

*Primary Examiner* — Unsu Jung
*Assistant Examiner* — James Moss
(74) *Attorney, Agent, or Firm* — Seed Intellectual Property Law Group LLP

(57) ABSTRACT

In one embodiment, a method to track the cardiac health of a patient is described. The method includes connecting to at least one motion sensor configured to sense movement of a patient and receiving motion data from the at least one motion sensor. The method further includes monitoring an activity level of the patient based at least in part on the motion data and detecting a change in the activity level of the patient based at least in part on the motion data. The method also includes altering a monitoring status of the cardiac health of the patient for a predetermined period of monitoring time based at least in part on the change in activity level.

21 Claims, 7 Drawing Sheets

(51) Int. Cl.

| | | |
|---|---|---|
| *A61B 5/11* | (2006.01) |
| *G16H 40/67* | (2018.01) |
| *G16H 50/70* | (2018.01) |
| *A61B 5/364* | (2021.01) |
| *G01C 22/00* | (2006.01) |
| *G16H 10/60* | (2018.01) |
| *G16H 50/30* | (2018.01) |

(52) U.S. Cl.

CPC ............ *A61B 5/6831* (2013.01); *A61B 5/746* (2013.01); *G16H 40/67* (2018.01); *G16H 50/70* (2018.01); *A61B 5/364* (2021.01); *G01C 22/006* (2013.01); *G16H 10/60* (2018.01); *G16H 50/30* (2018.01)

(56) References Cited

U.S. PATENT DOCUMENTS

| | | | |
|---|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov et al. |
| 7,212,850 B2 | 5/2007 | Prystowsky et al. |
| 7,559,902 B2 | 7/2009 | Ting et al. |
| 7,587,237 B2 | 9/2009 | Korzinov et al. |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky et al. |
| 7,941,207 B2 | 5/2011 | Korzinov |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0089538 A1* | 4/2006 | Cuddihy ............. A61B 5/0002 |
| | | 600/595 |
| 2006/0173499 A1 | 8/2006 | Hampton et al. |
| 2008/0312709 A1* | 12/2008 | Volpe ................... A61N 1/3987 |
| | | 607/6 |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0197353 A1* | 8/2012 | Donnelly ............... G16H 40/63 |
| | | 607/62 |
| 2012/0203491 A1* | 8/2012 | Sun ................... H04W 52/0219 |
| | | 702/108 |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0096447 A1* | 4/2013 | Dhawan ................. A61B 5/346 |
| | | 600/512 |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |

(56) References Cited

U.S. PATENT DOCUMENTS

| | | | |
|---|---|---|---|
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0126822 A1* | 5/2015 | Chavan | A61B 5/7275 |
| | | | 600/595 |
| 2015/0161554 A1 | 6/2015 | Sweeney et al. | |
| 2015/0297135 A1 | 10/2015 | Shoshani et al. | |
| 2015/0305675 A1* | 10/2015 | Miller | G16H 40/67 |
| | | | 600/301 |
| 2015/0328472 A1 | 11/2015 | Sullivan et al. | |
| 2016/0004831 A1 | 1/2016 | Carlson et al. | |
| 2016/0074667 A1* | 3/2016 | Sullivan | A61N 1/0484 |
| | | | 607/6 |
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |
| 2016/0113581 A1 | 4/2016 | Amir et al. | |
| 2016/0135706 A1* | 5/2016 | Sullivan | A61B 5/316 |
| | | | 600/509 |
| 2016/0256104 A1 | 9/2016 | Romem et al. | |
| 2016/0283900 A1 | 9/2016 | Johnson et al. | |
| 2016/0342761 A1* | 11/2016 | Whiting | G16H 10/60 |
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0040758 A1 | 2/2017 | Amir et al. | |
| 2017/0087371 A1* | 3/2017 | Freeman | A61B 5/721 |
| 2017/0162840 A1 | 6/2017 | Pendry | |
| 2017/0319862 A1 | 11/2017 | Foshee, Jr. et al. | |
| 2017/0367591 A1 | 12/2017 | Jorgensen | |
| 2018/0116537 A1 | 5/2018 | Sullivan et al. | |
| 2018/0116538 A1* | 5/2018 | Musley | A61B 5/316 |
| 2018/0117299 A1 | 5/2018 | Gustavson et al. | |
| 2018/0120892 A1* | 5/2018 | von Badinski | A61B 5/746 |
| 2018/0184933 A1 | 7/2018 | Sullivan et al. | |
| 2018/0185662 A1 | 7/2018 | Foshee, Jr. et al. | |
| 2018/0220901 A1* | 8/2018 | LeBoeuf | A61B 5/0816 |
| 2018/0243578 A1 | 8/2018 | Volosin | |
| 2018/0325466 A1* | 11/2018 | An | A61B 5/346 |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |
| 2020/0323452 A1* | 10/2020 | Mahajan | A61B 5/0022 |
| 2021/0128005 A1* | 5/2021 | Burnes | A61B 5/316 |
| 2021/0386312 A1* | 12/2021 | Chakravarthy | A61N 1/36542 |

FOREIGN PATENT DOCUMENTS

| | | |
|---|---|---|
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Helmut Klein et al., Risk stratification for implantable cardioverter defibrillator therapy: the role of the wearable cardioverter-defibrillator, European Heart Journal, vol. 34, Issue 29, Aug. 1, 2013, pp. 2230-2242, https://doi.org/10.1093/eurheartj/eht167, viewed on Aug. 11, 2023.*
"Decline in physical activity in the weeks preceding sustained ventricular arrhythmia in women" by Burch, et al. Heart Rhythm O2, vol. 1, No. 4, Oct. 2020.
Pagan-Carlo, et al., "Encircling Overlapping Multipulse Shock Waveforms for Transthoracic Defibrillation," JACC Journals, Dec. 1998, vol. 32 Issue 7, p. 2065-2071.
The LifeVest Network/Patient Data Management System, Zoll, 2015, May 3, 2000 Rev A.
Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
Lifecor LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Heartstart MRx and XL AED Algorithm—Application Note, Jul. 2001, Edition 2 Philips Healthcare, USA.
The LifeVest Network/Patient Data Management System, Zoll, 2015, 20C0503 Rev A.
Zoll, LifeVest, Proven protection from Sudden Cardiac Death, 2017, 4 pages. Pittsburgh PA, USA.
International Search Report and Written Opinion for PCT Application No. PCT/US2015/051726, dated May 20, 2016, European Patent Office, Rijswijk, 11 pages.

* cited by examiner

700

Receive activity data from a
remote device at predetermined
intervals                                    702

Project a trend of typical activity
level for the patient based at least
in part on the monitored activity
level                                        704

Notify patient of detected change
in activity trends                           706

MANAGING CARDIAC RISK BASED ON PHYSIOLOGICAL MARKERS

CROSS-REFERENCE TO RELATED PATENT APPLICATIONS

This patent application claims the benefit of U.S. Provisional Patent Application No. 63/129,547 filed Dec. 22, 2020, and is incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death quickly, e.g., within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest and continuously monitors the patient's intracardiac electrogram (IEGM). If certain heart arrhythmias are detected, the ICD delivers an electric shock through the heart.

As a further precaution, people who have been identified to have an increased risk of SCA are sometimes given a Wearable Cardioverter Defibrillator (WCD) system to wear until an ICD is implanted. Early versions of such systems were called wearable cardiac defibrillator systems. A WCD system typically includes a harness, vest, belt, or another garment that the patient wears. The WCD system further includes electronic components, such as a defibrillator and electrodes, coupled to the harness, vest, or another garment. When the patient wears the WCD system, the electrodes may electrically contact the patient's skin and aid in sensing the patient's electrocardiogram (ECG). If a shockable heart arrhythmia (e.g., ventricular fibrillation or VF) is detected from the ECG, the defibrillator delivers an appropriate electric shock through the patient's body, and thus through the heart. The delivered shock may restart the patient's heart and save the patient's life.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs and methods.

In one embodiment, a method to track the cardiac health of a patient is described. The method includes connecting to at least one motion sensor configured to sense movement of a patient and receiving motion data from the at least one motion sensor. The method further includes monitoring an activity level of the patient based at least in part on the motion data and detecting a change in the activity level of the patient based at least in part on the motion data. The method also includes altering a monitoring status of the cardiac health of the patient for a predetermined period of monitoring time based at least in part on the change in activity level.

In some embodiments, the method may include projecting a trend of typical activity level for the patient based at least in part on the monitored activity level. In some embodiments, the change in activity level may be a decrease in activity level from the trend of typical activity level of the patient. In some embodiments, the predetermined period of monitoring time may be at least two weeks. In some embodiments, the predetermined period of monitoring time may not exceed three weeks.

In some embodiments, the method may include receiving activity data from a remote device at predetermined intervals. In some embodiments, the predetermined intervals may be between one minute and twenty-four hours. In some embodiments, the method may include altering a time duration of detection of ventricular tachycardia for a predetermined period of time. In some embodiments, altering the time duration may include reducing the time duration to less than fifteen seconds. In some embodiments, the method may include returning to a normal monitoring status after a period of between one week and three weeks.

In some embodiments, the method may include detecting a number of premature ventricular contractions occurring over a daily time period and issuing an alert indicating the number of premature ventricular contractions detected combined with the detected change in activity level of the patient.

In another embodiment, a wearable cardiac monitoring system for monitoring health of a patient wearing the system is described. The system includes a support structure configured to be worn by a patient and an electronics module configured to be coupled to the support structure. The system also includes one or more processors in communication with the electronics module. The one or more processors are configured to cause the system to connect to at least one motion sensor configured to sense movement of a patient and receive motion data from the at least one motion sensor. The one or more processors are further configured to cause the system to monitor an activity level of the patient based at least in part on the motion data, detect a change in the activity level of the patient based at least in part on the motion data, and alter a monitoring status of the cardiac health of the patient for a predetermined period of monitoring time based at least in part on the change in activity level.

In some embodiments, the one or more processors may be configured to project a trend of typical activity level for the patient based at least in part on the monitored activity level. In some embodiments, the change in activity level may be a decrease in activity level from the trend of typical activity level of the patient. In some embodiments, the predetermined period of monitoring time may be at least two weeks. In some embodiments, the predetermined period of monitoring time may not exceed three weeks.

In some embodiments, the one or more processors may be configured to receive activity data from a remote device at predetermined intervals. In some embodiments, the predetermined intervals may be between one minute and twenty-four hours. In some embodiments, the one or more processors may be configured to alter a time duration of detection of ventricular tachycardia for a predetermined period of time. In some embodiments, altering the time duration may include reducing the time duration to less than fifteen seconds.

In some embodiments, the one or more processors may be configured to return to a normal monitoring status after a period of between one week and three weeks. In some embodiments, the one or more processors may be configured to detect a number of premature ventricular contractions occurring over a daily time period and issue an alert indicating the number of premature ventricular contractions detected combined with the detected change in activity level of the patient.

In one embodiment, a wearable cardiac monitoring system for monitoring health of a patient wearing the system is described. The system includes a support structure configured to be worn by a patient and an electronics module configured to be coupled to the support structure. The system also includes one or more displays proximate the electronics module and one or more processors in communication with the electronic module. The one or more processors are configured to cause the system to connect to at least one motion sensor configured to sense movement of a patient, receive motion data from the at least one motion sensor, and monitor an activity level of the patient based at least in part on the motion data. The one or more processors are further configured to cause the system to project a trend of typical activity level for the patient based at least in part on the monitored activity level and detect a change in the activity level of the patient based at least in part on the motion data and trend data. The one or more processors are also configured to cause the system to detect a number of premature ventricular contractions occurring over a daily time period, issue an alert indicating the number of premature ventricular contractions detected combined with the detected change in activity level of the patient, and alter a monitoring status of the cardiac health of the patient for a predetermined period of monitoring time based at least in part on the change in activity level.

BRIEF DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
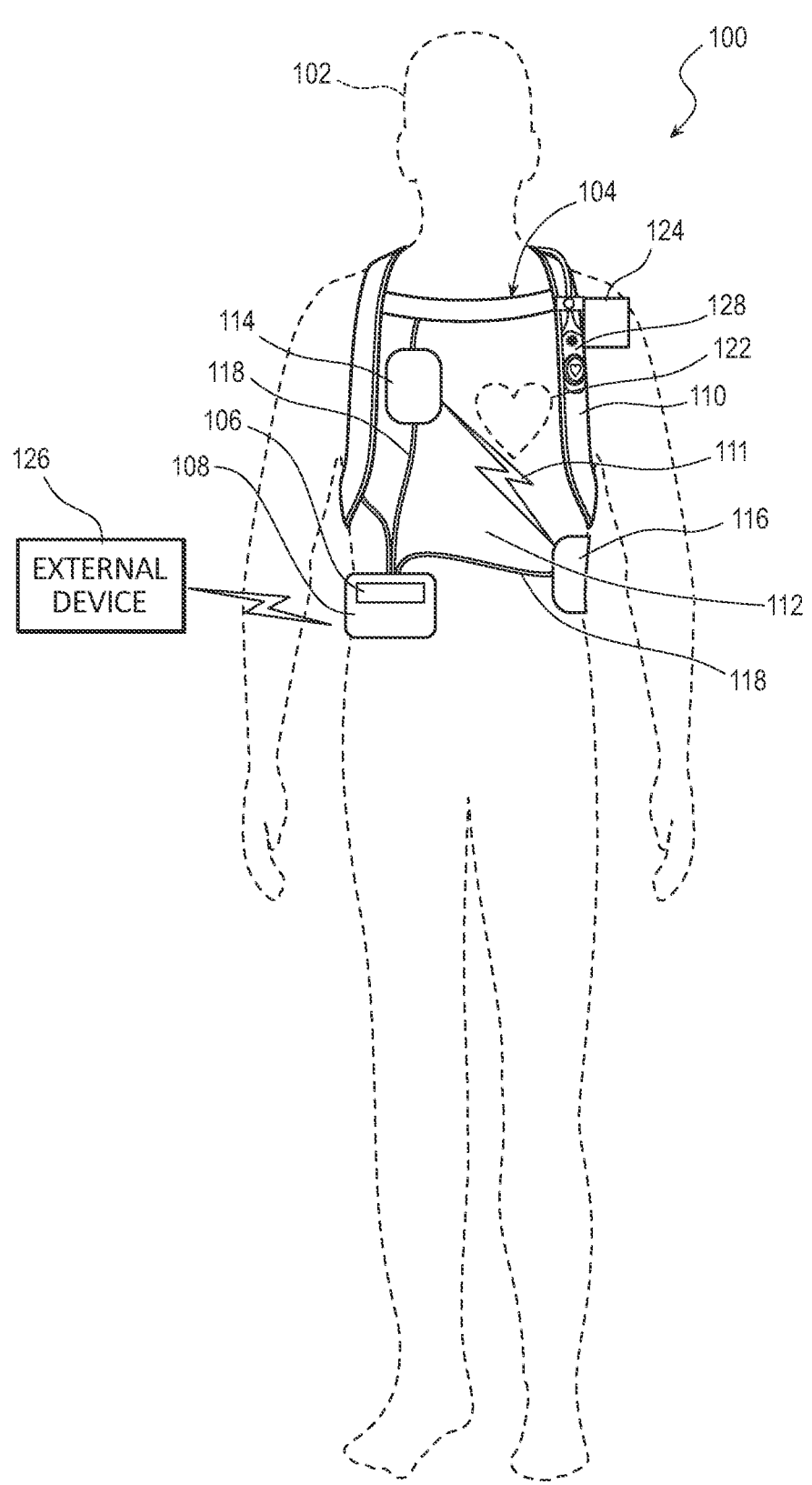
FIG. 1 is a diagram of a sample wearable cardiac monitoring system in accordance with exemplary embodiments described herein.

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present description includes examples of cardiac monitoring and treatment systems, such as a Wearable Cardiac Defibrillator (WCD) system and other wearable cardiac monitoring devices, as well as alert management systems and methods. The disclosure will discuss a WCD and provide examples using a WCD, but it will be understood that other systems can be used instead of a WCD.

Embodiments of wearable health monitoring systems include wearable ECG monitors, wearable vital sign monitoring systems, including temperature, blood pressure monitors, heart rate monitors, SPO2 detectors, step detectors, infusion pumps, etc. In some scenarios, such systems can be utilized alone or in combination with other devices, systems, or both. Furthermore, such devices, systems, or both can be supported by accessories, which can assist with data collection, transfer, trending as well as alerts. Such accessories can include tablets, mobile devices such as a cell phone or a watch.

Wearable Cardioverter Defibrillators (WCDs) are worn by patients at risk for sudden cardiac arrest. In some embodiments, activity sensor acquired data may be used to determine the likelihood of an event occurrence, potentially well in advance of the event (days, weeks, months). Predicting when an event may occur may enable early preventative or ameliorative actions and treatments.

The present disclosure offers medical monitoring system and methods configured to interface with activity data sensors to detect changes, such as activity decline and heighten or elevate monitoring, interactions with the patient, and management of a cardiac patient for a subsequent, recommended or determined period of time in which the patient may be at a heightened risk of a cardiac event.

In one instance, a decline in physical activity may be indicative of a cardiac event. For example, a certain population may experience a decline in physical activity about two weeks prior to a cardiac event. Therefore, when a decline in exercise levels is detected, the patient, caretaker, or both be notified to increase monitoring and adjust management of the cardiac condition for the following two to three weeks.

In one embodiment, a patient wears a WCD over a predetermined time period. The WCD acquires and transmits signals to a Central Care Station. The patient may also wear a smart device which may collect the patient's activity data over the predetermined time period. Alternatively, the WCD itself comprises an activity sensor, which aggregates activity data that can be accessed, viewed, and/or trended for any changes. For example, a smart device may access the activity data on the WCD embedded activity sensor. The accessed data can be transmitted in various ways, including, on a scheduled or cadence basis to the accessory, to a remote central care station, or a combination of the two where it can be viewed and evaluated for any changes warranting a heightened level of monitoring.

FIG. 1 illustrates a system 100 with a patient 102 wearing an example of a WCD system 104 according to embodiments described herein. In some embodiments, the WCD system 104 may include one or more communication devices 106, a support structure 110, and an external defibrillator 108 connected to two or more defibrillation electrodes 114, 116, among other components.

The support structure 110 may be worn by the patient 102. The patient 102 may be ambulatory, meaning the patient 102 can walk around and is not necessarily bed-ridden while wearing the wearable portion of the WCD system 104. While the patient 102 may be considered a "user" of the WCD system 104, this is not a requirement. For instance, a user of the WCD system 104 may also be a clinician such as a doctor, nurse, emergency medical technician (EMT), or other similarly tasked individual or group of individuals. In some cases, a user may even be a bystander. The particular context of these and other related terms within this description should be interpreted accordingly.

In some embodiments, the support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap or may be kept close to the patient 102 such as in a cart, bag, stroller, wheelchair, or other vehicle.

In some embodiments, the support structure 110 can be worn by being attached to the body of the patient 102 by adhesive material, for example as shown and described in U.S. Pat. No. 8,024,037, incorporated herein in its entirety by reference. In some embodiments, the support structure 110 can be implemented as described in U.S. Patent Publication No. 20170056682, incorporated herein in its entirety by reference. In still further embodiments, additional components of the WCD system 104 may incorporated in the housing of the support structure 110 instead of being attached externally to the support structure 110. One example is described in U.S. Patent Publication No. 20170056682, incorporated herein in its entirety by reference.

The external defibrillator 108 may be coupled to the support structure 110 or may be carried remotely from the patient 102. The external defibrillator 108 may be triggered to deliver an electric shock to the patient 102 when patient 102 wears the WCD system 104. For example, if certain thresholds are exceeded or met, the external defibrillator 108 may engage and deliver a shock to the patient 102.

The defibrillation electrodes 114, 116 can be configured to be worn by patient 102 in a number of ways. For instance, the defibrillator 108 and the defibrillation electrodes 114, 116 can be coupled to the support structure 110 directly or indirectly. For example, the support structure 110 can be configured to be worn by the patient 102 to maintain at least one of the electrodes 114, 116 on the body of the patient 102, while the patient 102 is moving around, etc. The electrodes 114, 116 can be thus maintained on the torso 112 by being attached to the skin of patient 102, simply pressed against the skin directly or through garments, etc. In some embodiments, the electrodes 114, 116 are not necessarily pressed against the skin but becomes biased that way upon sensing a condition that could merit intervention by the WCD system 104. In addition, many of the components of defibrillator 108 can be considered coupled to support structure 110 directly, or indirectly via at least one of defibrillation electrodes 114, 116.

The WCD system 104 may defibrillate the patient 102 by delivering an electrical charge, pulse, or shock 111 to the patient 102 through a series of electrodes 114, 116 positioned on the torso 112. For example, when defibrillation electrodes 114, 116 are in good electrical contact with the torso 112 of patient 102, the defibrillator 108 can administer, via electrodes 114, 116, a brief, strong electric pulse 111 through the body. The pulse 111 is also known as shock, defibrillation shock, therapy, electrotherapy, therapy shock, etc. The pulse 111 is intended to go through and restart heart 122, in an effort to save the life of patient 102. The pulse 111 can further include one or more pacing pulses of lesser magnitude to pace heart 122 if needed. The electrodes 114, 116 may be electrically coupled to the external defibrillator 108 via a series of electrode leads 118. The defibrillator 108 may administer an electric shock 111 to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116.

In some embodiments, the WCD system 104 may also include either an external or internal monitoring device or some combination thereof. FIG. 1 displays an external monitoring device 124 which may also be known as an outside monitoring device. The monitoring device 124 may monitor at least one local parameter. Local parameters may include a physical state of the patient 102 such as ECG, movement, heartrate, pulse, temperature, and the like. Local parameters may also include a parameter of the WCD 104, environmental parameters, or the like. For example, in some embodiments, the monitoring device 124 may include sensors to gather patient movement, ambient lighting, and the like. The monitoring device 124 may be physically coupled to the support structure 110 or may be proximate the support structure 110. In either location, the monitoring device 124 is communicatively coupled with other components of the WCD 104.

For some of these parameters, the device 124 may include one or more sensors or transducers. Each one of such sensors can be configured to sense a parameter of the patient 102, and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 102 are also referred to herein as patient physiological inputs and patient inputs. In some embodiments, a sensor can be construed more broadly as encompassing many individual sensors.

In some embodiments, a communication device 106 may enable the patient 102 to interact with, and garnish data from, the WCD system 104. The communication device 106 may enable a patient or third party to view patient data, dismiss a shock if the patient is still conscious, turn off an alarm, and otherwise engage with the WCD system 104. In some instances, the communication device 106 may transfer or transmit information include patient data to a third-party data server such as a cloud server or a blockchain server. In some embodiments, the communication device 106 may be a separable part of an external defibrillator 108. For example, the communication device 106 may be a separate device coupled to the external defibrillator 108. In some embodiments, the communication device 106 may be wired or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device 106. For example, the defibrillator 108 may include components able to communicate to the patient and the WCD system 104 may include a separate communication device 106 remote form the defibrillator 108.

In some embodiments, the communication device 106 may be communicatively coupled to an alert button 128. The alert button 128 may be removably coupled to the support structure 110. The patient 102 may couple the alert button 128 to the support structure 110 or may couple the alert button 128 to an article of clothing. The alert button 128 may have a wired connection or be wirelessly connected to the communication device 106. In some embodiments, the alert button 128 may include a visual output, an audio output, and a user input. The visual output may include a light, such as an LED, a small screen, or some combination thereof. Likewise, the audio output may include one or more speakers. The output of the audio output may be loud enough to be heard over nominal background noise. In some embodiments, the audio output might have an adjustable volume range. In some embodiments, the alert button 128 may include a microphone. In still further embodiments, the alert button 128 may also include a haptic response.

In some embodiments, the defibrillator 108 may connect with one or more external devices 126. For example, as shown in FIG. 1, the defibrillator 108 may connect to various external devices 126 such as the cloud, a remote desktop, a laptop, a mobile device, or other external device using a network such as the Internet, local area networks, wide area networks, virtual private networks (VPN), other communication networks or channels, or any combination thereof.

In embodiments, one or more of the components of the exemplary WCD system 104 may be customized for the patient 102. Customization may include a number of aspects including, but not limited to, fitting the support structure 110 to the torso 112 of patient 102; baseline physiological parameters of patient 102 can be measured, such as the heart rate of patient 102 while resting, while walking, motion detector outputs while walking, etc. The measured values of such baseline physiological parameters can be used to customize the WCD system to make its analysis more accurate since patients' bodies differ from one another. Of course, such parameter values can be stored in a memory of the WCD system and the like. Moreover, a programming interface can be made according to embodiments, which receives such measured values of baseline physiological parameters. Such a programming interface may input automatically in the WCD system these, along with other data.

Figure 2:
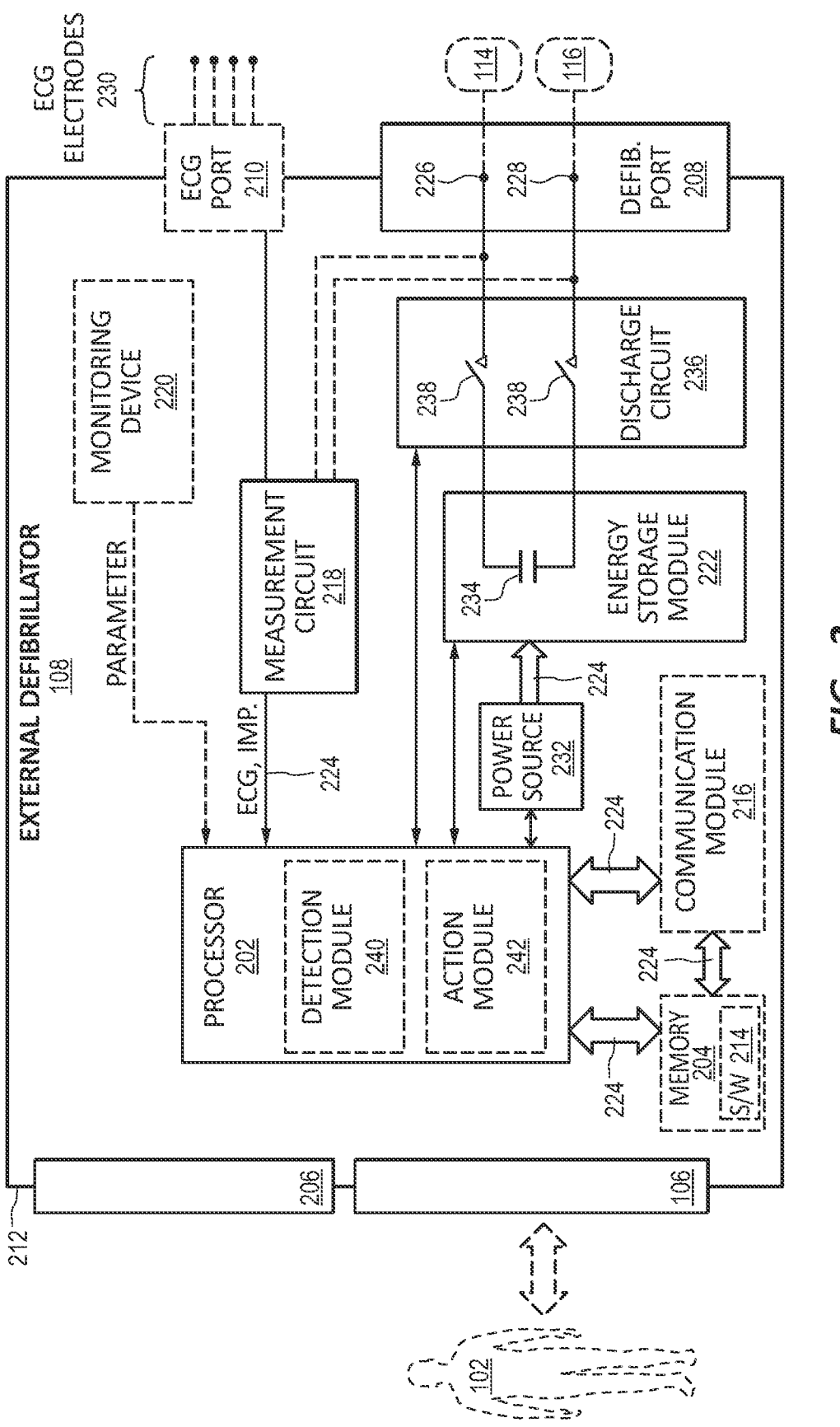
FIG. 2 is a block diagram of an example wearable cardiac monitoring device in accordance with exemplary embodiments described herein.

FIG. 2 is a diagram displaying various components of an example external defibrillator 108. The external defibrillator 108 may be an example of the defibrillator 108 described with reference to FIG. 1. The components shown in FIG. 2 may be contained within a single unit or may be separated amongst two or more units in communication with each other. The defibrillator 108 may include a communication device 106, processor 202, memory 204, defibrillation port 208, and ECG port 210, among other components. In some embodiments, the components are contained within a housing 212 or casing. The housing 212 may comprise a hard shell around the components or may comprise a softer shell for increased patient comfort.

The communication device 106, processor 202, memory 204 (including software/firmware code (SW) 214), defibrillation port 208, ECG port 210, communication module 216, measurement circuit 218, monitoring device 220, and energy storage module 222 may communicate, directly or indirectly, with one another via one or more buses 224. The one or more buses 224 may allow data communication between the elements and/or modules of the defibrillator 108.

The memory 204 may include random access memory (RAM), read only memory (ROM), flash RAM, and/or other types. The memory 204 may store computer-readable, computer-executable software/firmware code 214 including instructions that, when executed, cause the processor 202 to perform various functions (e.g., determine shock criteria, determine heart rate, issue shock command, issue alerts, etc.). In some embodiments, the processor 202 may include an intelligent hardware device, e.g., a central processing unit (CPU), a microcontroller, an application-specific integrated circuit (ASIC), etc.

In some embodiments, the memory 204 can contain, among other things, the Basic Input-Output system (BIOS) which may control basic hardware and/or software operations such interactions and workings of the various components of the defibrillator 108, and in some embodiments, components external to the defibrillator 108. For example, the memory 204 may contain various modules to implement the workings of the defibrillator 108 and other aspects of the present disclosure.

In some embodiments, the defibrillator 108 may include a user interface 206. The user interface 206 may be in addition to or part of the communication device 106. The user interface 206 may display an ECG of the patient, a status of the defibrillator 108, a status of a charge (e.g., a battery charge or an energy storage module), and the like.

In some embodiments, the user interface 206 may include output devices, which may include visual, audible, or tactile, for communicating to a user by outputting images, sounds or vibrations. Images, sounds, vibrations, and an alert or notification that can be perceived by a person is also called human-perceptible indications (HPIs). Output devices, or HPIs, may include a light(s), a screen to display what is sensed, detected and/or measured, speakers, and the like. In some embodiments, the screen may provide visual feedback to a third party for their resuscitation attempts and treatment plans. In some embodiments, the speaker may be configured to issue voice prompts, beeps, loud alarm sounds and/or words to warn bystanders, etc.

In some embodiments, the user interface 206 may further include input devices for receiving inputs from users. Such input devices may include various controls, such as push-buttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

In some embodiments, the defibrillator 108 may include a defibrillation port 208. The defibrillation port 208 may comprise a socket, opening, or electrical connection in the housing 212. In some instances, the defibrillation port 208 may include two or more nodes 226, 228. The two or more nodes 226, 228 may accept two or more defibrillation electrodes (e.g., defibrillation electrodes 114, 116, FIG. 1). The nodes 226, 228 may provide an electrical connection between the defibrillation electrodes 114, 116 and the defibrillator 108. The defibrillation electrodes 114, 116 may plug into the two or more nodes 226, 228 via one or more leads (e.g., leads 118), or, in some instances, the defibrillation electrodes 114, 116 may be hardwired to the nodes 226, 228. Once an electrical connection is established between the defibrillation port 208 and the electrodes 114, 116, the defibrillator 108 may be able to deliver an electric shock to the patient 102.

In some embodiments, the defibrillator 108 may include an ECG port 210 in the housing 212. The ECG port 210 may accept one or more ECG electrodes 230 or ECG leads. In some instances, the ECG electrodes 230 sense a patient's ECG signal. For example, the ECG electrodes 230 may record electrical activity generated by heart muscle depolarization, timing, or both. The ECG electrodes 230 may utilize 4-leads to 12-leads or multichannel ECG, or the like. The ECG electrodes 230 may connect with the patient's skin.

In some embodiments, the defibrillator 108 may include a measurement circuit 218. The measurement circuit 218 may be in communication with the ECG port 210. For example, the measurement circuit 218 may receive physiological signals from ECG port 210. The measurement circuit 218 may additionally or alternatively receive physiological signals via the defibrillation port 208 when defibrillation electrodes 114, 116 are attached to the patient 102. The measurement circuit 218 may determine a patient's ECG signal from a difference in voltage between the defibrillation electrodes 114, 116.

In some embodiments, the measurement circuit 218 may monitor the electrical connection between the defibrillation electrodes 114, 116 and the skin of the patient 102. For example, the measurement circuit 218 can detect impedance between electrodes 114, 116. The impedance may indicate the effective resistance of an electric circuit. An impedance calculation may determine when the electrodes 114, 116 have a good electrical connection with the patient's body.

If, in some embodiments, the defibrillator 108 lacks a sensor port, the measurement circuit 218 may obtain physiological signals through nodes 226, 228 when defibrillation electrodes 114, 116 are attached to the patient. The input may reflect an ECG measurement. The patient parameter can be an ECG, which can be sensed as a voltage difference between electrodes 114, 116. In addition, the patient parameter may be an impedance, which may be sensed between electrodes 114, 116 and/or between the connections of sensor port considered pairwise. In some embodiments, the impedance may be used to determine when electrodes 114, 116 and/or sensing electrodes are not making good electrical contact with the patient's body.

In some embodiments, the defibrillator 108 may include an internal monitoring device 220 within the housing 212. The monitoring device 220 may monitor at least one local parameter. Local parameters may include physical state of the patient such as ECG, movement, heartrate, pulse, temperature, and the like. Local parameters may also include a parameter of the WCD system (e.g., WCD 104, FIG. 1), defibrillator 108, environmental parameters, or the like.

In some embodiments, the WCD system 104 may include an internal monitoring device 220 and an external monitoring device (e.g., external monitoring device 124). If both monitoring devices 124, 220 are present, the monitoring devices 124, 220 may work together to parse out specific parameters depending on position, location, and other factors. For example, the external monitoring device 124 may monitor environmental parameters while the internal monitoring device 220 may monitor patient and system parameters.

Patient parameters may include patient physiological parameters. Patient physiological parameters may the WCD system in detecting when the patient is in need of a shock or other intervention or assistance. Patient physiological parameters may also include the patient's medical history, event history, and the like. Examples of such parameters may include the patient's ECG, blood oxygen level, blood flow, blood pressure, blood perfusion, pulsatile change in light transmission or reflection properties of perfused tissue, heart sounds, heart wall motion, breathing sounds and pulse.

The internal and external monitoring devices 220, 124 may include one or more sensors configured to acquire patient physiological signals. For example, either one or both monitoring devices 220, 124 may include one or more electrodes to detect ECG data, a perfusion sensor, a pulse oximeter, a device for detecting blood flow (e.g., a Doppler device), a sensor for detecting blood pressure (e.g., a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on.

In some embodiments, the local parameter is a trend that can be detected in a monitored physiological parameter of patient. A trend can be detected by comparing values of parameters at different times over short and long terms. Parameters whose detected trends can particularly help a cardiac rehabilitation program may include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. The report may aid a physician in monitoring the progress of patient.

In some embodiments, the monitoring devices 220, 124 may include sensors that monitor external conditions. For example, the monitoring devices may monitor environmental parameters. Environmental parameters may include ambient temperature, pressure, humidity, and the like.

In some embodiments, the defibrillator 108 may include a power source 232. The power source 232 may comprise a battery or battery pack, which may be rechargeable. In some instances, the power source 232 may comprise a series of different batteries to ensure the defibrillator 108 has power. For example, the power source 232 may include a series of rechargeable batteries as a prime power source and a series of non-rechargeable batteries as a secondary source. If the patient 102 is proximate an AC power source, such as when sitting down, sleeping, or the like, the power source 232 may include an AC override wherein the power source 232 draws power from the AC source.

In some embodiments, the defibrillator 108 may include an energy storage module 222. The energy storage module 222 may store electrical energy in preparation or anticipation of providing a sudden discharge of electrical energy to the patient. In some embodiments, the energy storage module 222 may have its own power source and/or battery pack. In other embodiments, the energy storage module 222 may pull power from the power source 232. In still further embodiments, the energy storage module 222 may include one or more capacitors 234. The one or more capacitors 234 may store an electrical charge, which may be administered to the patient. The processor 202 may be communicatively coupled to the energy storage module 222 to trigger the amount and timing of electrical energy to provide to the defibrillation port 208 and, subsequently, the patient 102.

In some embodiments, the defibrillator 108 may include a discharge circuit 236. The discharge circuit 236 may control the energy stored in the energy storage module 222. For example, the discharge circuit 236 may either electrical couple or decouple the energy storage module 222 to the defibrillation port 208. The discharge circuit 236 may be communicatively coupled to the processor 202 to control when the energy storage module 222 and the defibrillation port 208 should or should not be coupled to either administer or prevent a charge from emitting from the defibrillator 108. In some embodiments, the discharge circuit 236 may include on or more switches 238. In further embodiments, the one or more switches 238 may include an H-bridge.

In some embodiments, the defibrillator 108 may include a communication module 216. The communication module 216 may establish one or more communication links with either local hardware and/or software to the WCD system 104 and defibrillator 108 or to remote hardwire separate from the WCD system 104. In some embodiments, the communication module 216 may include one or more antennas, processors, and the like. The communication module 216 may communicate wirelessly via radio frequency, electromagnetics, local area networks (LAN), wide area networks (WAN), virtual private networks (VPN), RFID, Bluetooth, cellular networks, and the like. The communication module 216 may facilitate communication of data and commands such as patient data, episode information, therapy attempted, CPR performance, system data, environmental data, and so on. In some embodiments, the communication module 216 may include a display screen to display messages to the patient. In some embodiments, the display screen may be a touch screen, backlit screen, passive, reflective LCD screen or the like.

In further embodiments, the communication module 216 may include one or more LEDs which may also be used to convey information to the patient. In some embodiments, the LED brightness may be modulated, the LEDs may be color changing, and the like. In some embodiments, if multiple LEDs are present, each LED may represent various bits of information. For example, one LED may represent heartrate information and enable the patient to quickly determine their heart is operating normally. Another LED may represent the heartrate signal to ensure the patient the heartrate readings are being properly transmitted. Another LED may also represent system status and allow the patient to easily ascertain that the system is fully functioning.

In some embodiments, the processor 202 may execute one or more modules. For example, the processor 202 may execute a detection module 240 and/or an action module 242. The detection module 240 may be a logic device or algorithm to determine if any or a variety of thresholds are exceeded which may require action of the defibrillator 108. For example, the detection module 240 may receive and interpret all of the signals from the ECG port 210, the defibrillation port 208, the monitoring device 220, an external monitoring device, and the like. The detection module 240 may process the information to ensure the patient is still conscious and healthy. If any parameter indicates the patient 102 may be experiencing distress or indicating a cardiac episode, the detection module 240 may activate the action module 242.

The action module 242 may receive data from the detection module 240 and perform a series of actions. For example, an episode may merely be a loss of battery power at the power source 232 or the energy storage module 222, or one or more electrodes (e.g., ECG electrodes, defibrillation electrodes) may have lost connection. In such instances, the action module 242 may trigger an alert to the patient or to an outside source of the present situation. This may include activating an alert module. If an episode is a health risk, such as a cardiac event, the action module 242 may begin a series of steps. This may include issuing a warning to the patient, issuing a warning to a third party, priming the energy storage module 222 for defibrillation, releasing one or more conductive fluids proximate defibrillation electrodes 114, 116, and the like.

Figure 3:
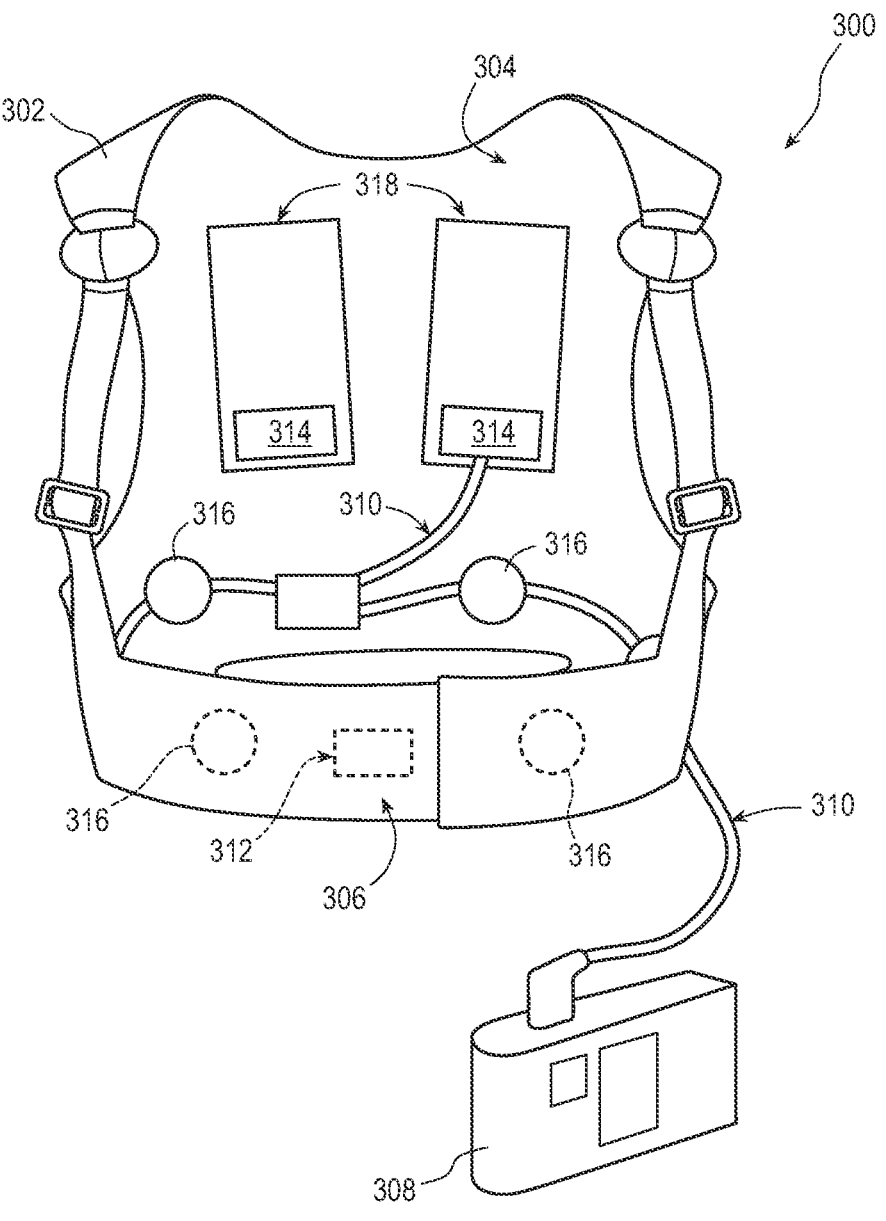
FIG. 3 is a diagram of sample embodiments of components of a wearable cardiac monitoring system in accordance with exemplary embodiments described herein.

FIG. 3 is a diagram of sample embodiments of components of a WCD system 300 according to exemplary embodiments. The WCD system 300 may be an example of the WCD system 104 describe with reference to FIG. 1. In some embodiments, the WCD system 300 may include a support structure 302 comprising a vest-like wearable garment. In some embodiments, the support structure 302 has a back side 304, and a front side 306 that closes in front of a chest of the patient.

In some embodiments, the WCD system 300 may also include an external defibrillator 308. The external defibrillator 308 may be an example of the defibrillator 108 describe with reference to FIGS. 1 and 2. As illustrated, FIG. 3 does not show any support for the external defibrillator 308, but as discussed, the defibrillator 308 may be carried in a purse, on a belt, by a strap over the shoulder, and the like as discussed previously. One or more wires 310 may connect the external defibrillator 308 to one or more electrodes 312, 314, 316. Of the connected electrodes, electrodes 312, 314 are defibrillation electrodes, and electrodes 316 are ECG sensing electrodes.

The support structure 302 is worn by the patient to maintain electrodes 312, 314, 316 on a body of the patient. For example, the back-defibrillation electrodes 314 are maintained in pockets 318. In some embodiments, the inside of the pockets 318 may comprise loose netting, so that the electrodes 314 can contact the back of the patient. In some instances, a conductive fluid may be deployed to increase connectivity. Additionally, in some embodiments, sensing electrodes 316 are maintained in positions that surround the patient's torso, for sensing ECG signals and/or the impedance of the patient.

In some instances, the ECG signals in a WCD system 300 may comprise too much electrical noise to be useful. To ameliorate the problem, multiple ECG sensing electrodes 316 are provided, for presenting many options to the processor (e.g., processor 202, FIG. 2). The multiple ECG sensing electrodes 316 provide different vectors for sensing the ECG signal of the patient.

Figure 4:
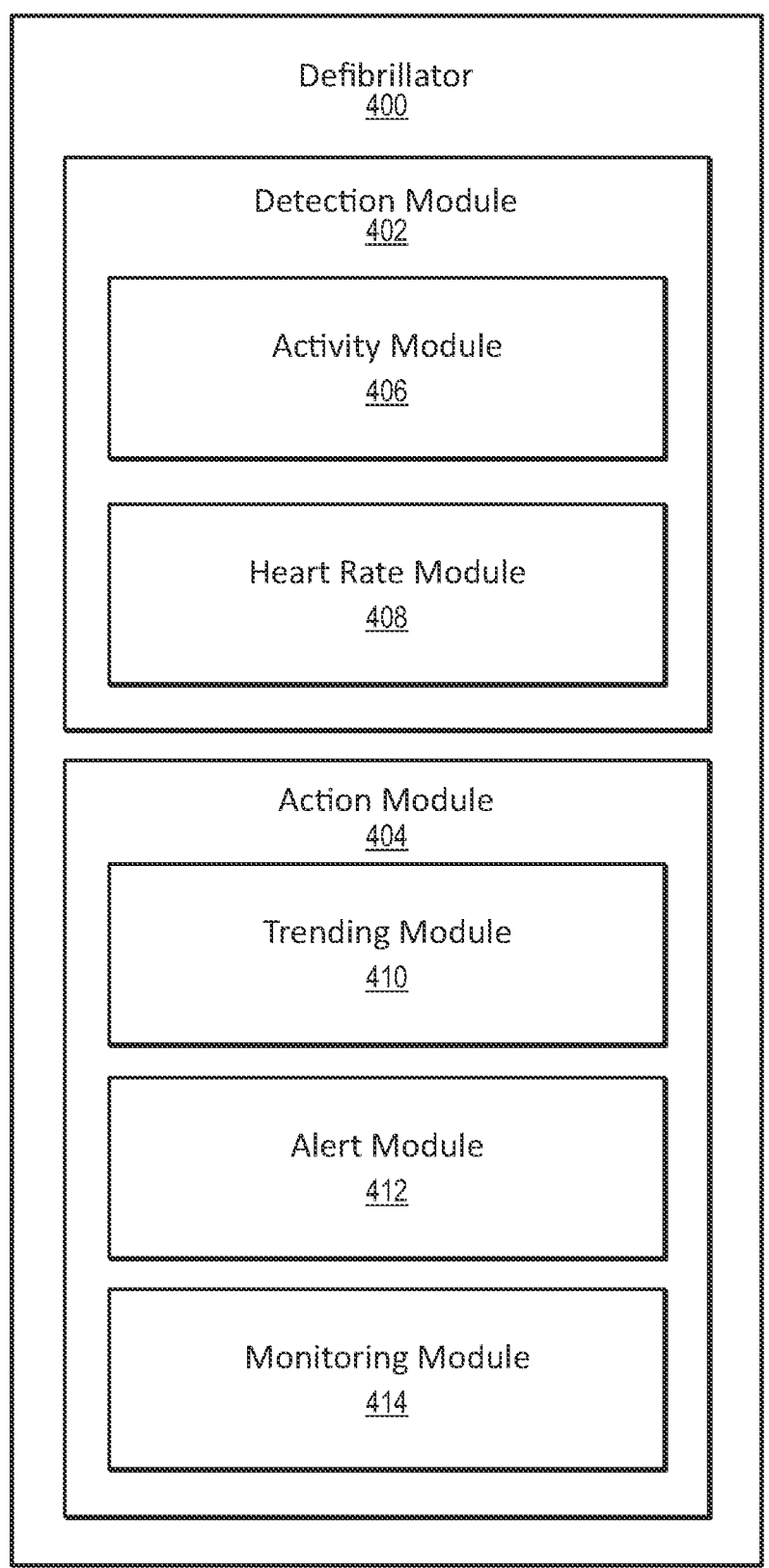
FIG. 4 is a block diagram of an example wearable cardiac monitoring device in accordance with exemplary embodiments described herein.

FIG. 4 is a block diagram illustrating components of one example of a defibrillator 400. The defibrillator 400 may be an example of the defibrillator 108 described with reference to FIGS. 1 and 2 and defibrillator 308 described with reference to FIG. 3. In this example, the defibrillator 400 has a detection module 402 and an action module 404. The detection module 402 and action module 404 may be examples of the detection module 240 and action module 242 described with reference to FIG. 2. In some embodiments, the detection module 402 may include an activity module 406, a heart rate module 408, or some combination thereof. In some embodiments, the action module 404 may include a trending module 410, an alert module, a monitoring module 414, or some combination thereof.

The detection module 402 may aid in the prediction of a cardiac event. For example, the activity module 406 may track and record the physical exertion of the patient. This may include tracking daily activity, mapping patterns, and the like. The activity module 406 may couple to and communicate with one or more movement sensors, heart rate sensors, or other sensors and data collection methods that track physical exertion. The activity module 406 may track information such as workout regimes, step counts, elevate heart rate durations, and the like.

In some embodiments, the detection module 402 may communicate with various sensors proximate the WCD device and may also connect with various sensors and devices external to the WCD. For example, the detection module 402 may communicate with external monitoring devices (e.g., external monitoring device 124, FIG. 1) or with other external devices (e.g., external device 126). Some external devices may include smart phones, smart watches, fitness trackers, heart rate monitors, IoT devices, or other biometric device trackers.

In some embodiments, the detection module 402 may ping various sensors requesting movement data. The movement data may comprise steps, posture, breathing rate, perceived exertion, and the like. In some embodiments, the movement data may comprise a recorded workout such as a bicycle ride, dancing, weight lifting, swimming, or other activities that may not be tracked strictly by steps. The movement data may include snapshot information such as total length of workout, total amount of steps per day or other time frame, increased respiration rate for a time duration, and the like. In other embodiments, the activity data may be more minute and finite. For example, it may track the movement along with time day and send this information to the action module 404.

The heart rate module 408 may track and record the heart rates of the patient. For example, the heart rate module 408 may communicate with various electrodes (e.g., electrodes 316, FIG. 3) to garnish the heart rate of the patient. For example, the heart rate module 408 may receive and interpret signals received from the ECG port, defibrillation port, an external monitoring device, and the like. The heart rate module 408 may process the data to determine a cardiac status of the patient. For example, the heart rate module 408 may determine if the patient is healthy and conscious, if a patient is exercising, if a patient has a normal heartbeat, if a patient is resting, and the like. The heart rate module 408 may also analyze the data for a shockable rhythm or any other irregularities. In some embodiments, the heart rate module 408 may communicate with external devices to collect heart rate data.

In some embodiments, based at least in part on information and data from the detection module 402, the action module 404 may take one or more actions. For example, in some embodiments, the action module 404 may have a trending module 410, an alert module 412, and a monitoring module 414.

The trending module 410 may track various physical activity trends from the data collected by the activity module 406. For example, the trending module 410 may track daily trends, weekly trends, and monthly trends. The trending module 410 may track when there are significant changes in activity levels. In some embodiments, the trending module 410 may determine changes over a predetermined period of time. For example, the trending module 410 may determine if a patient has a significant change in their behavior. The trending module 410 may compare current activity level for the selected time period to a predetermined time period to determine if there is a significant change in activity level. In some instances, the trending module 410 may compare a 24-hour time period to a previous 5-day, 7-day, 10-day, 12-day period, or some variation thereof. In some embodiments, the time periods may be predetermined. In other embodiments, the time periods may be specific to a patient. In still further embodiments, the trending module 410 may complete multiple comparisons to determine various changes in activity behaviors.

The alert module 412 may cause one or more alerts to issue. For example, the alert module 412 may cause a safety alarm, a physiological alarm, a system alarm, or any other alarm related to the WCD to issue. The alert may have multiple components. For example, the alert may have a multi-visual component, an audible component, and a haptic component. The multi-visual component may include a light(s), a visual display including a GUI, or some combination thereof. The visual component may use the light(s) to garnish the attention of the user and may display a written message or coded message on a screen.

In some embodiments, the alert module 412 may issue an alert to the patient, caregiver, medical personnel, or some combination thereof concerning a noticeable reduce in activity levels. Given activity levels may preempt a cardiac event, the personnel may review the alert to determine any necessary actions. In some embodiments, the action may trigger the monitoring module 414 to adjust its monitoring of the patient.

In some embodiments, notifications regarding activity level changes can further be generated to the patient not meeting their activity level along with notifications to the medical professional. For example, trending notifications can inform the patient that they are trending up or down or are behind their target rate, time, or level. Similarly, notifications to the clinic and provide information on how much a patient is behind their average or normalized target activity levels.

For example, the monitoring module 414 may have one or more levels of monitoring. A baseline level of monitoring may be a standard patient with an expected cardiac risk. The monitoring module 414 may have a heightened monitoring level which may adjust alerts and trend thresholds to watch the cardiac condition of the patient more carefully. In one embodiment, the monitoring module 414 may reduce the threshold for recording and issuing an alert for ventricular tachycardia (VT). For example, VT may have a threshold of approximately fifteen (15) seconds. Once VT has been detected for a duration of 15 or more seconds, the monitoring module 414 may issue an alert and record and event. In a heightened state, the VT threshold may be reduced to less than fifteen seconds. So for example, once VT has been detected for ten (10) seconds, the monitoring module may issue an alert and record the event.

In another embodiment, the monitoring module 414 may have a lower threshold for tracking premature ventricular contractions (PVC). A PVC counter may indicate a cranky or unhealthy heart which may be pre-symptomatic of a cardiac event. The threshold for issuing an alert for a PVC total count may be reduced in order to provide additional scrutiny for the patient's cardiac health.

Figure 5:
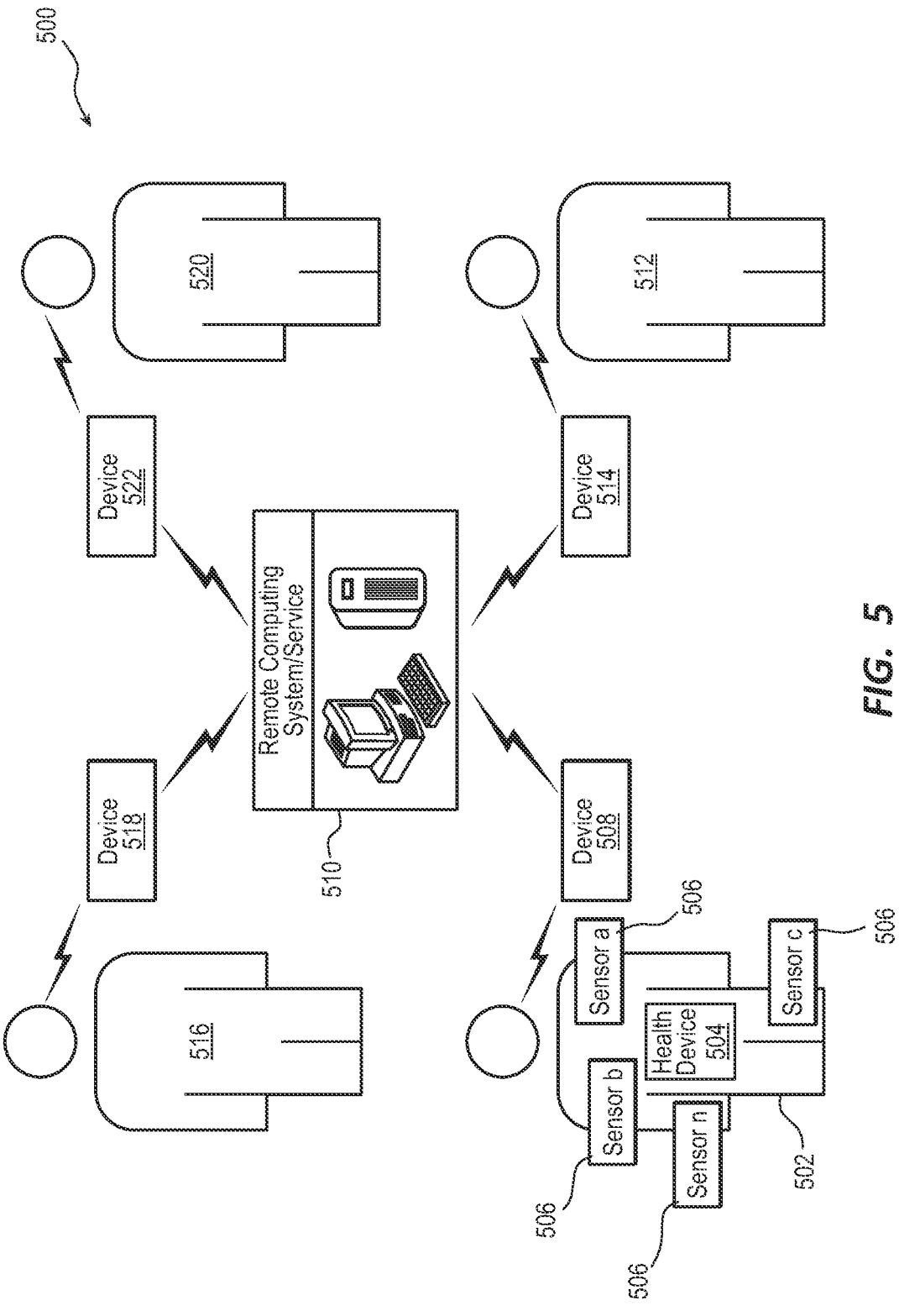
FIG. 5 is a diagram of a sample health care system in accordance with exemplary embodiments described herein.

FIG. 5 is a schematic of a system 500 in which a health monitoring station 510 may communicate with various entities. The health monitoring station 510 may communicate with various devices 508, 514, 518, 522 coupled to various entities 502, 512, 516, 520 to communicate and share data and information regarding a patient 502.

For example, the patient 502 may be wearing a health device 504. One or more sensors 506 proximate the patient 502 may in communication with the health device 504. The health device 504 may be one of a WCD (e.g., WCD 104, 300 described with reference to FIGS. 1 & 3), defibrillator (e.g., defibrillator 108 described with reference to FIGS. 1 and 2 and defibrillator 308 described with reference to FIG. 3), Holter monitor, MCOT, MCT, and the like. The health device 504 may be a wearable device which may be positioned and utilized for data acquisition and tracking of patient movement and health.

In some embodiments, the health device 504 may contain one or more sensors for data acquisition. In further embodiments, the health device 504 may couple to other one or more remote sensors 506 proximate the patient 502. In some embodiments, the sensors 506 may be in communication with the health device 504 and send data to the health device 504.

In some embodiments, the health device 504 may be in communication with a device 508. The device 508, as well as devices 514, 516, 522, may include one or more smart devices such as a smart watch, a mobile phone, a tablet, a laptop, a computer, or another device capable of communicating over the Internet. The device 508 may be a personal device of the patient 502 and may be in communication with the health device 504. In some embodiments, the health device 504 may transmit information to the device 508. The information may be raw data or may be filtered data collected from the one or more sensors 506. In some embodiments, the mobile device 508 may request the data transfer from the health device 504. The periodicity of data transfer may be predetermined intervals or may be adjusted based on the patient's health status.

The mobile device 508 may transfer the patient's data, raw or filtered, to a remote computing system 510 also called the "Central Care System." The Central Care System 510 may collect and process patient data, including movement data. Other relevant personnel such as one or more user experts 516, 520, or caregivers 512 may access the Central Care System through one or more of their devices 518, 522, 514 respectively.

Figure 6:
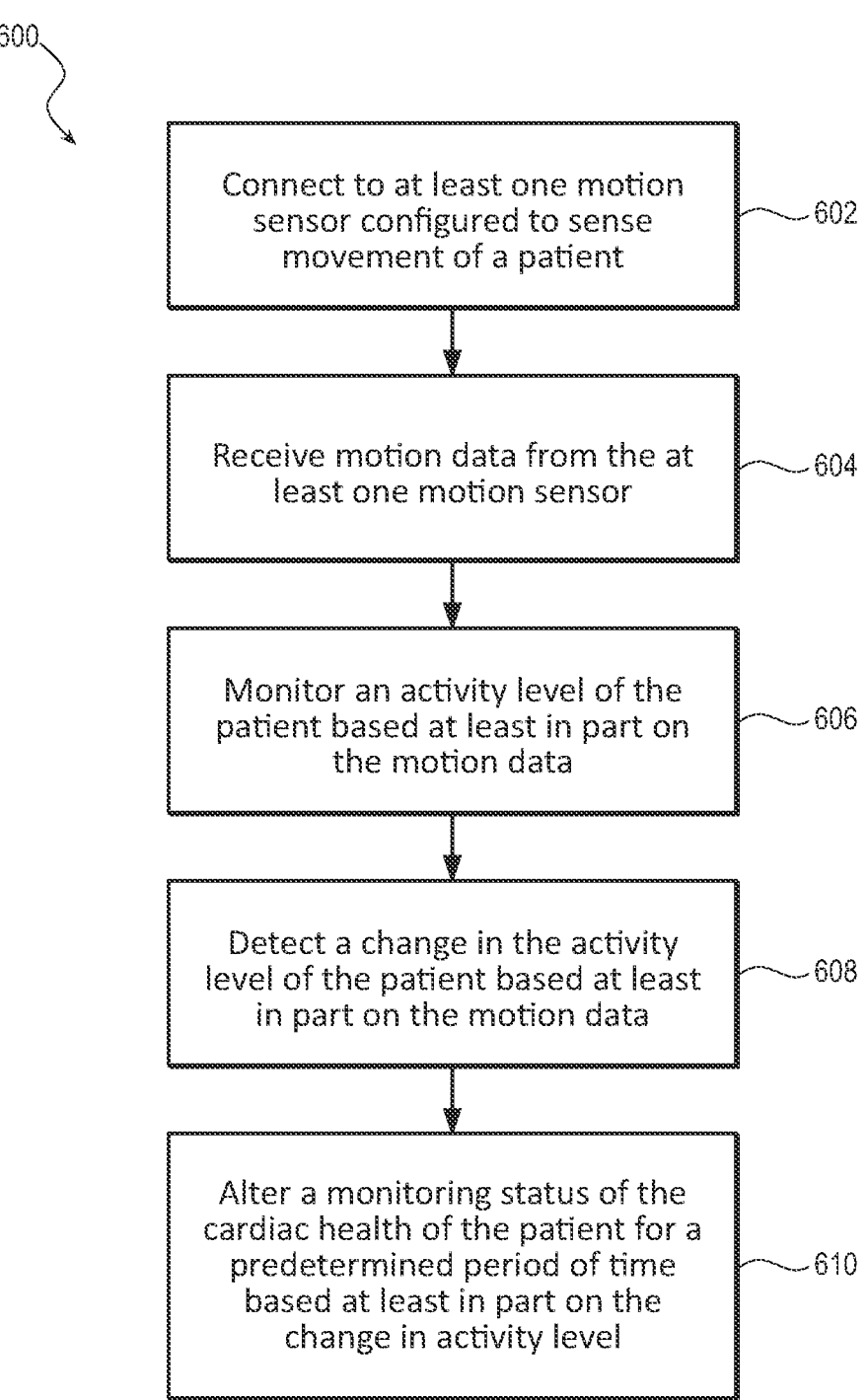
FIG. 6 is a flow diagram in accordance with exemplary embodiments described herein.

FIG. 6 is a flow chart illustrating an example of a method 600 for WCD systems, in accordance with various aspects of the present disclosure. For clarity, the method 600 is described below with reference to aspects of one or more of the systems described herein.

At block 602, the method 600 may connect to at least one motion sensor configured to sense movement of a patient. For example, the at least one sensor may comprise at least one of an accelerometer, tilt sensor, shock sensor, triple axis accelerometer, multi-axis accelerometer, gyroscope, vibration sensor, impact sensor, or some combination thereof. In some embodiments, the sensors may be a part of a mobile device or health device wearable by the patient.

At block 604, the method 600 may receive motion data from the at least one motion sensor. The motion data may include information such as steps, aerobic activity level, duration of aerobic activity, and the like. In some embodiments, the motion data may include recorded workouts or events entered by the patient. The motion data may be raw data or filtered data. The motion data may also include time stamps.

At block 606, the method 600 may include monitoring an activity level of the patient based at least in part on the motion data. For example, some patients may experience a decrease in activity levels prior to experiencing a cardiac event. The method 600 may collect and track the patient's activity levels on a rolling basis to establish trends and routines. Once the patient has an established baseline of activity level, the method 600 may, at block 608, tract the data to detect a change in the activity level of the patient based at least in part on the motion data. The change in activity level may include a decrease in activity. The decrease in activity may be a percentage lower than normal activity levels. For example, the patient may experience a 10-90% decrease in activity level. In some embodiments, the lower activity levels may be triggered by life events such as hospital visits, travel considerations, injuries, and the like. However, withstanding any extenuating circumstances, an unexplained decrease in activity level may be an early indicator of a cardiac event.

At block 610, the method 600 may include altering a monitoring status of the cardiac health of the patient for a predetermined period of time based at least in part on the detected change in activity level. For example, the cardiac health of the patient may have different monitoring levels. Some examples may include an ordinary standard monitoring level, a heightened monitoring level, and a lower monitoring level. In some embodiments, a heightened monitoring level may change the threshold alarm of ventricular ectopy. For example, in a normal monitoring state, ventricular ectopy monitoring begins at approximately the fifteen (15) second threshold of VT above 170. In a heightened monitoring state, the ventricular ectopy monitoring may be reduced to shorten the detection time and track shorter runs of VT. The shorter episodes may be between five (5) seconds and fifteen (15) seconds of VT. In some embodiments, the shortened duration of VT may be set for a predetermined period of time. The predetermined period of time may be between one day and three weeks. In some embodiments, the predetermined period of time may be approximately two weeks. If a cardiac event has not occurred, or if the patient has returned to a normal activity level with satisfactory heart rhythms, the VT duration may return to a standard detection time.

In some embodiments, the monitoring status may also monitor premature ventricular contractions (PVC). Once the monitoring status meets a threshold, a PVC counter may begin detecting the number of premature heart beats. The quantity and duration of premature heart beats may indicate an irritable cardiac condition, which when coupled with a decrease in activity level, could indicate a higher risk of a cardiac event and a heightened monitoring status, medical care, or some combination thereof.

Thus, the method 600 may provide for one method of monitoring a patient's cardiac health and well-being. It should be noted that the method 600 is just one implementation and that the operations of the method 600 may be rearranged or otherwise modified such that other implementations are possible.

Figure 7:
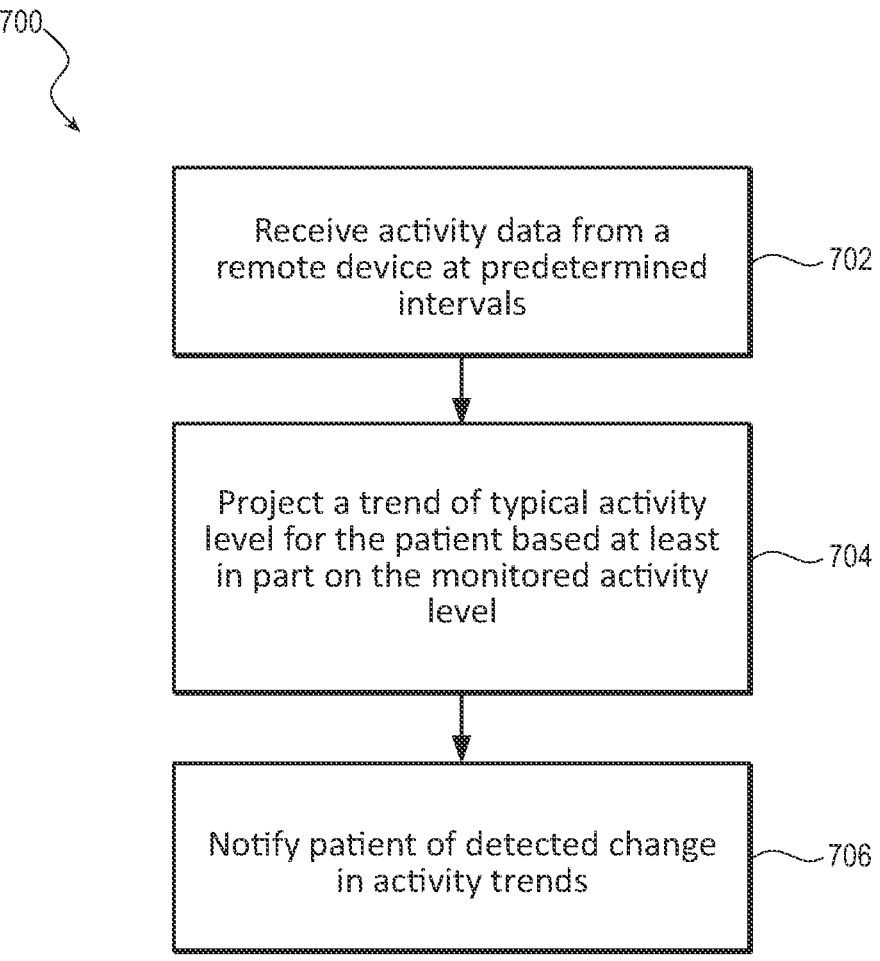
FIG. 7 is a flow diagram in accordance with exemplary embodiments described herein.

FIG. 7 is a flow chart illustrating an example of a method 700 for WCD systems, in accordance with various aspects of the present disclosure. For clarity, the method 700 is described below with reference to aspects of one or more of the systems described herein.

At block 702, the method 700 may include receiving activity data from a remote device at predetermined intervals. For example, in some embodiments, the method 700 may ping the remote device at routine intervals to request activity data. In other embodiments, the remote device might push data at routine intervals. The routine intervals may be predetermined time intervals such as daily, weekly, hourly, or the like. In some embodiments, the routine intervals may be altered due to increased or decreased monitoring of the patient.

At block 702, the method 700 project a trend of typical activity for the patient based at least in part on the monitored activity level. The trend of typical activity level may include an accumulated total time of predetermined activity level each day. For example, the patient may typically accumulate an approximate amount or range of steps each day. The patient may typically perform select activities around the house or have a perceived exertion rate apparent in a tracked respiration rate that may indicate a level of exercise. The patient may have a daily trend, a weekly trend, or some combination thereof. By learning the routine of the specific patient and their habits, the method 700 may better track the patient's typical activity level to determine when there is a change in that level of activity.

At block 702, the method 700 may notify the patient, caregiver, medical staff, or some combination thereof of a change in activity trends. The notification may be sent to all concerned parties at once or may initially send an alert to the patient and caregiver. In some embodiments, the patient, caregiver, or both may have the option to respond to the detected change in activity level. For example, the parties may respond with a cause for a reduced activity level such as illness, travel, job change, injury, or the like. The parties may also have the option to respond with the indication that there is no cause or correlation for the decreased activity level. Once the information from the patient and/or caregiver is received, the method 700 may send the change in activity level and correlation to medical personnel. This may alert the medical personnel to be more watchful of the patient's heart data as it is gathered in the Central Care Station.

Thus, the method 700 may provide for one method of monitoring a patient's cardiac health and well-being. It should be noted that the method 700 is just one implementation and that the operations of the method 700 may be rearranged or otherwise modified such that other implementations are possible.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method to track cardiac health of a patient, the method comprising:
receiving, by a processor, motion data from at least one motion sensor configured to sense movement of the patient;
monitoring, by the processor, an activity level of the patient based at least in part on the motion data;
detecting, by the processor, a decrease in the activity level of the patient based at least in part on the motion data, wherein the decrease in the activity level is detected upon comparing the activity level to a baseline activity level;
in response to detecting the decrease in the activity level, increasing, by the processor, a frequency that monitoring status information corresponding to the monitored activity level is received from a cardiac monitor, wherein the monitoring status information includes at least one cardiac measurement of the patient;
detecting, by the processor, a number of premature ventricular contractions in the monitoring status information upon increasing the frequency of the monitoring status information;
comparing, by the processor, the number of premature ventricular contractions to a threshold number of premature ventricular contractions; and
in response to detecting the decrease in the activity level and a determination that the number of premature ventricular contractions meets or exceeds the threshold number of premature ventricular contractions, decreasing, by the processor, a threshold for issuing an alert indicating a cardiac anomaly.

2. The method of claim 1, further comprising:
projecting, by the processor, a trend of typical activity level for the patient based at least in part on the monitored activity level.

3. The method of claim 2, wherein the decrease comprises a decrease in the activity level from the trend of the typical activity level of the patient.

4. The method of claim 1, wherein the decrease is observed over a predetermined period of monitoring.

5. The method of claim 1, wherein the cardiac monitor comprises a remote device.

6. The method of claim 5, wherein the frequency that the monitoring status information is received from the cardiac monitor is between one minute and twenty-four hours.

7. The method of claim 1, wherein:
the cardiac anomaly is ventricular tachycardia (VT), and
the threshold comprises a time duration of detection of the VT.

8. The method of claim 7, wherein the time duration is less than fifteen seconds.

9. The method of claim 1, further comprising:
resetting the frequency after a period of time between one week and three weeks.

10. The method of claim 1, further comprises:
issuing, by the processor, the alert indicating the number of premature ventricular contractions detected.

11. The method of claim 1, further comprising determining analyzing a heart rate associated with the at least one cardiac measurement of the patient for a shockable rhythm.

12. A system for monitoring health of a patient wearing the system, the system comprising:
a cardiac monitor; and
one or more processors configured to be in communication with the cardiac monitor, wherein the one or more processors are collectively configured to:
receive motion data from at least one motion sensor configured to sense movement of the patient,
monitor an activity level of the patient based at least in part on the motion data,
detect a decrease in the activity level of the patient based at least in part on the motion data, wherein the decrease in the activity level is detected upon comparison of the activity level to a baseline activity level,
in response to the detection of the decrease in the activity level, increase a frequency that monitoring status information corresponding to the monitored activity level is received from the cardiac monitor, wherein the monitoring status information includes at least one cardiac measurement of the patient,
detect a number of premature ventricular contractions in the monitoring status information upon increasing the frequency of the monitoring status information,
compare the number of premature ventricular contractions to a threshold number of premature ventricular contractions; and
in response to the detection of the decrease in the activity level and a determination that the number of premature ventricular contractions meets or exceeds the threshold number of premature ventricular contractions, decrease a threshold for issuing an alert indicating a cardiac anomaly.

13. The system of claim 12, wherein the one or more processors are further collectively configured to:
project a trend of typical activity level for the patient based at least in part on the activity level monitored.

14. The system of claim 13, wherein the decrease comprises a decrease in the activity level from the trend of the typical activity level of the patient.

15. The system of claim 12, wherein the decrease is observed over a predetermined period of monitoring time.

16. The system of claim 12, wherein the one or more processors are further collectively configured to:
transmit the monitoring status information to a remote device.

17. The system of claim 16, wherein the frequency that the monitoring status information is received from the cardiac monitor is between one minute and twenty-four hours.

18. The system of claim 12, wherein the one or more processors are further collectively configured to:
reset the frequency after a period of time between one week and three weeks.

19. The system of claim 12, wherein the one or more processors are further collectively configured to:

issue the alert indicating the number of premature ventricular contractions detected combined with the decrease in the activity level of the patient.

20. A system for monitoring health of a patient wearing the system, the system comprising:

a cardiac monitor;

one or more displays proximate the cardiac monitor; and one or more processors configured to be in communication with the cardiac monitor, the one or more processors are collectively configured to:

receive motion data from at least one motion sensor configured to sense movement of the patient, monitor an activity level of the patient based at least in part on the motion data, project a trend of typical activity level for the patient based at least in part on the monitored activity level, detect a decrease in the activity level of the patient based at least in part on the motion data and trend data, wherein the decrease in the activity level is detected upon comparison of the activity level and the trend data to a baseline activity level, in response to the detection of the decrease in the activity level, increase a frequency that monitoring status information corresponding to the monitored activity level is received from the cardiac monitor, wherein the monitoring status information includes at least one cardiac measurement of the patient, detect a number of premature ventricular contractions in the monitoring status information upon increasing the frequency of the monitoring status information, compare the number of premature ventricular contractions to a threshold number of premature ventricular contractions; and in response to the detection of the decrease in the activity level and a determination that the number of premature ventricular contractions meets or exceeds the threshold number of premature ventricular contractions, decrease a threshold for issuing an alert indicating a cardiac anomaly.

21. The system of claim 12, wherein the one or more processors further analyze a heart rate associated with the at least one cardiac measurement of the patient for a shockable rhythm.

* * * * *